United States Patent [19]

Lautenschläger et al.

[11] 4,349,686
[45] Sep. 14, 1982

[54] 5-(N-ALKYL-N-ACYL-AMINO)-THIOPHEN-2-CARBOXYLIC ACID DERIVATIVES

[75] Inventors: Hans-Heiner Lautenschläger, Pulheim-Stommeln; Hans Betzing, Kerpen-Horrem; Johannes Winkelmann, Cologne; Manfred Probst, Frechen; Brigitte Stoll, Pulheim, all of Fed. Rep. of Germany

[73] Assignee: A. Nattermann & Cie GmbH, Cologne, Fed. Rep. of Germany

[21] Appl. No.: 320,608

[22] Filed: Nov. 12, 1981

[51] Int. Cl.³ .................... C07D 333/24; A61K 31/38
[52] U.S. Cl. ........................................ 549/69; 424/275
[58] Field of Search ............................................ 549/69

[56] References Cited

U.S. PATENT DOCUMENTS 3,823,161 7/1974 Lesser .................................. 549/69
4,082,771 4/1978 Evans et al. ......................... 549/69

Primary Examiner—Alan Siegel
Attorney, Agent, or Firm—Pearne, Gordon, Sessions, McCoy & Granger

[57] ABSTRACT

The present invention refers to new 5-(N-Alkyl-N-acyl-amino)-thiophen-2-carboxylic acid derivatives having the general formula I

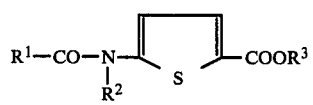

6 Claims, No Drawings

5-(N-ALKYL-N-ACYL-AMINO)-THIOPHEN-2-CARBOXYLIC ACID DERIVATIVES

The present invention is related to new 5-(N-alkyl-N-acyl)-amino-thiophen-2-carboxylic acid derivatives of the general formula I

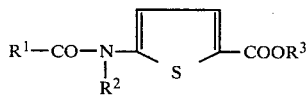

wherein
$R^1$ is an alkyl group having from 1 to 5 carbon atoms,
$R^2$ is an alkyl group having from 12 to 18 carbon atoms,
$R^3$ is a hydrogen, an alkali ion or an alkyl group having from 1 to 3 carbon atoms,
as well as process for producing the same and pharmaceutical preparations containing the same as active ingredient.

The hydrocarbon groups $R^1$, $R^2$ and $R^3$ may be straight or branched, saturated or unsaturated groups. $R^1$ preferably are stragiht or branched saturated hydrocarbon groups, in particular straight alkyl groups. $R^2$ preferably are straight saturated or such hydrocarbon groups with 12 to 18 carbon atoms having one olefine doublebond.

The compounds according to the present invention show interesting pharmacological properties. The new compounds have both anti-inflammatory and lipid decreasing properties. The acylamino thiophen carboxylic acids of the present invention have anti-inflammatory activity both in vitro and in vivo. They furthermore show an advantageous inhibation of the complement system. Furthermore, they decrease the platelet aggregation. These valuable pharmacological properties are furthermore supplemented by a significant plaques reduction in animals, a decrease of the total cholesterol, an increase of the α-lipoproteins and a reduction of the β-lipoproteins.

Thus, the N-alkyl-N-acyl-amino-thiophen carboxylic acid derivatives may in particular be used for the treatment of inflammatory, arteriosclerotic and thrombotic diseases. Their use in dosages ranging from 1 to 500 mg/kg, in particular 10 to 300 mg/kg and most preferably from 20 to 200 mg/kg.

The acylamino thiophen carboxylic acid derivatives according to the present invention may be used as free acids or as the alkali salts thereof or as the esters of $C_{1-3}$-alcohols as active agent in pharmaceutical preprations together with usual carrier materials or dilluents. Esters of alcohols with 1 to 3 carbon atoms are particularly useful for oral administration.

The acylamino thiophen carboxylic acids and their derivatives are mostly produced by processes the chemical reaction whereof is known as such. The starting materials of the present process are the known carboxylic acid amides of the general formula II

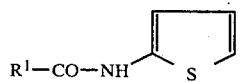

wherein $R^1$ has the same meaning as in formula I. The compounds of formula II are alkylated at the nitrogen atom in accordance with the chemical reaction described by W. STEINKOFF, Liebigs Ann. vol. 403, p. 17. According to the present invention, the sodium there used is preferably substituted by sodium hydride and the reaction is carried out in a polar aprotic solvent such as methyl ethyl ketone or dimethylformamide. The addition of an alkali methyl iodide is preferred when using slowly reacting halogenides. The resulting product are compounds of the general formula III

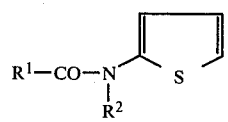

wherein $R^1$ and $R^2$ have the same meaning as in formula I. These compounds then are further converted into the aldehydes of the general formula IV

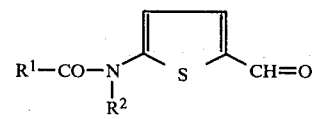

wherein $R^1$ and $R^2$ have the same meaning as in formula I, applying reaction conditions usual for the FILSMEYER formylation. When oxydizing the aldehydes of formula IV with usual oxydizing agents such as potassium permanganate in an aqueous organic solvent, the new acids of formula I

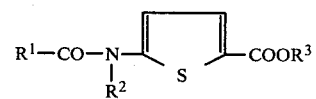

wherein $R^3$ is hydrogen, are obtained.

The free acids of formula I ($R^3$=H) may be converted to their alkali methyl salts wherein $R^3$ is alkali, by subjecting the acids to reaction with an alkali methyl hydroxide or carbonate in an aqueous or alcoholic-aqueous solvent and recovering the salts by evaporating the resulting solution.

The salts of formula I wherein $R^3$ is an alkali, may be converted into the corresponding esters of formula I with $R^3$ being an $C_{1-3}$-alkyl, by alkylating the salts with a alkyl halide or a similar alkylating agent having the formula V $$R^3-X \qquad V$$

wherein $R^3$ is a straight or branched $C_{1-3}$-alkyl group and X is a halogen such as Cl, Br, J or another usual group readily split of during alkylation, in a polar aprotic solvent. On the other side, esters of the formula I wherein $R^3$ is alkyl, may also be produced by subjecting the acids of formula I with $R^3$ being hydrogen or their alkali salts with $R^3$ being alkali, at first to reaction with thionyl chloride, possibly in an organic solvent, and further reaction with an alcohol of the formula $R^3$—OH, $R^3$ having the same meaning as in formula I.

Suitable substituted acid amides of formula II are for instance:
N-(2-thienyl)-acetamide,
N-(2-thienyl)-propionic acid amide, N-(2-thienyl)-butyric acid amide,
N-(2-thienyl)-valerianic acid amide,
N-(2-thienyl)-capronic acid amide.

For preparing the compounds of formula III from the compounds of formula II there may be used as alkylating agent of formula $R^2$—X for instance: bromododecane, bromotridecane, bromotetradecane, bromopentadecane, bromohexadecane, bromoheptadecane, bromooctadecane and the corresponding chloro and iodo compounds.

The full synthesis is further explained with some of the compounds III and IV and the resulting final compounds of formula I. Melting points given in the following examples have been determined by means of a Büchi-510-melting point determining apparatus and are not corrected melting points. IR-spectra have been determined by means of a Perkin-Elmer 257 and the mass spectra by means of a Varian MAT-311A (70 eV).

EXAMPLE 1

N-hexadecyl-N-(2-thienyl)-acetamide. 21 g N-(2-thienyl)-acetamide are dissolved in 150 cc. anhydrous methylethylketon. 3.6 g of sodium hydride are added to this solution. After termination of hydrogen formation, 38.9 g of chlorohexadecane and 44.7 g of dry sodiumiodide are added thereto and the reaction mixture is heated to boiling for 24 hours. The reaction mixture is evaporated in a vacuum and the residue is treturated with water and ether. The ethereal layer is separated, washed with water and dried over $Na_2SO_4$. The solvent is evaporated and the residue is purified chromatographically on a column of silicic acid gel using hexan-/ethyl acetate as eluant.

Yield: 28 g (51% of the theoretical), m.p.: 34°–36° C. IR (KBr): 1675 $cm^{-1}$

EXAMPLE 2

N-hexadecyl-N-(2-thienyl)-propionic acid amide. 7.9 g of sodium hydride are added to a solution of 46.5 g of N-(2-thienyl)-propionic acid amide in 600 cc. of anhydrous dimethylformamide (DMF). The mixture is stirred until termination of hydrogen formation. Thereafter, 78 g of chlorohexadecane and 9 g of dry sodium iodide are added thereto and the reaction mixture is heated to 80° C. for 24 hours. After cooling, the reaction mixture is poured upon water, the mixture is extracted with ether and the ethereal layer is washed with water and dried over $Na_2SO_4$. The ether is evaporated in a vacuum and the residue is purified chromatographically on a column of silicic acid gel using hexane/ethyl acetate as eluant.

Yield: 75 g (66% of the theoretical), m.p.: 36° C. IR (KBr): 1680 $cm^{-1}$

EXAMPLE 3

N-hexadecyl-N-(2-thienyl)-butyric acid amide. 8.6 g of sodium hydride are added to a solution of 55 g of N-(2-thienyl)-butyric acid amide dissolved in 600 cc. of anhydrous DMF. The mixture is stirred until termination of hydrogen formation. Thereafter, 84.7 g of chlorohexadecane and 9.7 g of sodium iodide are added thereto and the reaction mixture is heated to 80° C. for 24 hours. After cooling, the reaction mixture is poured into water, the mixture is extracted with ether, the ethereal layer is separated, washed with water and dried over $Na_2SO_4$. The ether is evaporated in a vacuum and the residue is purified chromatographically on a column of silicic acid gel using hexan/ethyl acetate as eluant.

Yield: 78 g (61% of the theoretical), m.p.: 36° C. IR (KBr): 1675 $cm^{-1}$

EXAMPLE 4

N-(5-Formyl-thien-2-yl)-N-hexadecyl-acetamide. 27 g of N-Hexadecyl-N-(2-thienyl)-acetamide are dissolved in 22 cc. of anhydrous DMF and 14 g of phosphorus oxychloride are added dropwise thereto under cooling with ice, thereby avoiding increase of the temperature of the reaction mixture above 20° C. Stirring is continued for 1 hour at 20° C. and the reaction mixture finally is stirred for 3 hours at 80° C. Ice is added to the reaction mixture and 5 N soda lye is added thereto until reaching a pH of 6. The resulting mixture is extracted with ether, the ethereal phase is separated, washed with water and dried over $Na_2SO_4$. The ether is separated and the residue is purified chromatographically on a column of silicic acid gel using hexane/ethyl acetate as eluant.

Yield: 25 g (86% of the theoretical), m.p.: 53° C.

EXAMPLE 5

N-(5-Formyl-thien-2-yl)-N-hexadecyl-propionic acid amide. 75 g of N-hexadecyl-N-(2-thienyl)-propionic acid amide are dissolved in 59 cc. of anhydrous DMF and 36.7 g of phosphorus oxychloride are added thereto dropwise with ice cooling such that the temperature of the reaction mixture does not increase above 20° C. Stirring is continued for 1 hour and 20° C. and the reaction mixture finally is heated 3 hours to 80° C. Ice is added to the reaction mixture and 5 N soda lye is added until reaching a pH of 6. The resulting mixture is extracted with ether, the ethereal layer is separated, washed with water and dried over $Na_2SO_4$. The desired final product crystallizes at low temperature from the ethereal solution.

Yield: 57.8 g (72% of the theoretical), m.p.: 78° C.

EXAMPLE 6

N-(5-Formyl-thien-2-yl)-N-hexadecyl-butyric acid amide. 78 g of N-hexadecyl-N-(2-thienyl)-butyric acid amide are dissolved in 59 cc. of anhydrous DMF and 36.7 g of phosphorus oxychloride are added thereto with ice cooling such that the temperature of the reaction mixture does not rise above 20° C. Stirring is continued for 1 hour at 20° C. and the mixture is finally heated for 3 hours to 80° C. Ice is added to the reaction mixture and 5 N soda lye is added until reaching a pH of 6. The mixture is extracted with ether, the ethereal layer is separated, washed with water and dried over $Na_2SO_4$. The desired final product crystallizes from the ethereal solution upon cooling to low temperature.

Yield: 58 g (70% of the theoretical), m.p.: 66°–67° C.

As described in Examples 4 to 6 there are further produced:
N-(5-formyl-thien-2-yl)-N-hexadecyl-valerianic acid amide,
N-(5-formyl-thien-2-yl)-N-hexadecyl-capronic acid amide.

EXAMPLE 7

N-Acetyl-N-hexadecyl-5-amino-thien-2-yl-carboxylic acid. 25 g of N-(5-formyl-thien-2-yl)-N-hexadecylacetamide are dissolved in 20 cc. of pyridine. A solution of 6.7 g of potassium permanganate in 90 cc. of pyridine and 40 cc. of water is added with stirring and cooling such that the temperature of the reaction mixture does not rise above $-3°$ C. Stirring is continued until all of KMnO₄ has been reacted. Thereafter, the solvents are distilled off, the residue is triturated with dilute hydrochloric acid and the mixture is extracted with chloroform. The chloroform layer is separated, washed with water and dried over Na₂SO₄. The solvent is evaporated and the resulting crude product is purified chromatographically on a column of silicic acid gel using chloroform as eluant.

Yield: 8.4 g (32% of the theoretical), m.p.: 82° C. MS (m/e): 409 (42%); 367 (100%); 156 (31%); 43 (13%).

EXAMPLE 8

N-Hexadecyl-N-propionyl-5-amino-thien-2-yl-carboxylic acid. 57.8 g of N-(5-formyl-thien-2-yl)-N-hexadecyl-propionic acid amide are dissolved in 300 cc. of pyridine. A solution of 14.6 g of KMnO₄ in 198 cc. of pyridine and 85 cc. of water is added with stirring and cooling such that the temperature of the reaction does not rise above −3° C. Stirring is continued until all of KMnO₄ has been reacted. Thereafter, the solvent is distilled off, the residue is triturated with dillued acid and the mixture is extracted with chloroform. The chloroform layer is separated, washed with water and dried over Na₂SO₄. The solvent is evaporated and the resulting crude product is purified chromatographically on a column of silicic acid gel using chloroform as eluant.

Yield: 14.5 g (24% of the theoretical), m.p.: 88°–89° C. MS (m/e): 423 (20%); 367 (100%); 156 (24%).

EXAMPLE 9

N-Butyryl-N-hexadecyl-5-amino-thien-2-yl-carboxylic acid. 58 g of N-(5-formyl-thien-2-yl)-N-hexadexyl-butyric acid amide are dissolved in 300 cc. of pyridine. A solution of 13.9 g of KMnO₄ in 177 cc. of pyridine and 82 cc. of water are added thereto dropwise with stirring and cooling such that the temperature of the reaction mixture does not rise above −3° C. Stirring is continued until all of KMnO₄ has been reacted. The solvents are distilled off, the residue is trituated with dillued hydrochloric acid and the reaction mixture is extracted with chloroform. The chloroform layer is separated, washed with water and dried over Na₂SO₄. The solvent is evaporated and the remaining crude product is purified chromatographically on a column of silicic acid gel using chloroform as eluant.

Yield: 10.0 g (17% of the theoretical), m.p.: 79°–81° C. MS (m/e): 437 (14%); 367 (100%); 156 (17%); 71 (16%).

As described in Examples 7 to 9 there are further more produced:
N-Hexadecyl-N-valeryl-5-amino-thien-2-yl-carboxylic acid,
N-Hexadecyl-N-hexanoyl-5-amino-thien-2-yl-carboxylic acid.

EXAMPLE 10

Sodium salt of N-acetyl-N-hexadecyl-5-amino-thien-2-yl-carboxylic acid.

N-Acetyl-N-hexadecyl-5-amino-thien-2-yl-carboxylic acid as dissolved in ethanol and neutralized with alcoholic soda lye. The mixture is evaporated to dryness in a vacuum and the solid residue is powdered. IR (KBr): 1575, 1670 cm⁻¹.

As described in Example 10 there are produced the sodium salt of the following acids:
N-Hexadecyl-N-propionyl-5-amino-thien-2-yl-carboxylic acid,
N-Butyryl-N-hexadecyl-5-amino-thien-2-yl-carboxylic acid,
N-Hexadecyl-N-valeryl-5-amino-thien-2-yl-carboxylic acid,
N-Hexadecyl-N-hexanoyl-5-amino-thien-2-yl-carboxylic acid.

EXAMPLE 11

N-Hexadecyl-N-propionyl-5-amino-thien-2-yl carboxylic acid methyl ester.

1 g of the sodium salt of N-hexadecyl-N-propionyl-5-amino-thien-2-yl-carboxylic acid are suspended in 20 cc. of acetone. 0.8 g of methyl iodide are added dropwise thereto. The mixture is refluxed for 5 hours, the solvent is distilled off and the residue is dissolved in chloroform. The chloroform solution is washed consecutively with an aqueous solution of NaHCO₃ and water and thereafter is dried over Na₂SO₄. The solvent is distilled off and the residue is purified chromatographically on a column of silicic acid gel using hexane/ethyl acetate as eluant.

Yield: 0.2 g (20% of the theoretical), m.p.: 52° C. IR (KBr): 1710 and 1665 cm⁻¹. MS (m/e): 437 (23%); 406 (1%); 381 (100%); 170 (25%).

What we claim is:

1. 5-(N-Alkyl-N-acyl-amino)-thiophen-2-carboxylic acid derivatives having the general formula I

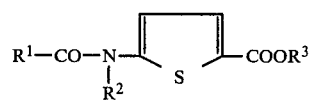

wherein
R¹ is an alkyl group having from 1 to 5 carbon atoms,
R² is an alkyl group having from 12 to 18 carbon atoms,
R³ is hydrogen, alkali or an alkyl group having from 1 to 3 carbon atoms.

2. 5-(N-Acetyl-N-hexadecyl)-amino-thien-2-yl carboxylic acid and the pharmarceutically compatible salts and esters thereof according to claim 1.

3. 5-(N-Hexadecyl-N-propionyl)-amino-thien-2-yl carboxylic acid and the pharmaceutically compatible salts and esters thereof according to claim 1.

4. 5-(N-Butyryl-N-hexadecyl)-amino-thien-2-yl carboxylic acid and the pharmaceutically compatible salts and esters thereof according to claim 1.

5. 5-N-Hexadecyl-N-valeryl)-amino-thien-2-yl carboxylic acid and the pharmaceutically compatible salts and esters thereof according to claim 1.

6. 5-N-(Hexadecyl-N-hexanoyl)-amino-thien-2-yl carboxylic acid and the pharmaceutically compatible salts and esters thereof according to claim 1.

* * * * *